United States Patent [19]

Shibatani et al.

[11] Patent Number: 5,204,248

[45] Date of Patent: Apr. 20, 1993

[54] PROCESS FOR PREPARING 2-HALOGENO-3-HYDROXY-3-PHENYL-PROPIONIC ACID ESTER COMPOUNDS

[75] Inventors: Takeji Shibatani, Kobe; Takuo Nishida, Amagasaki; Hiroaki Matsumae, Kobe, all of Japan

[73] Assignee: Tanabe Seiyaku Co., Ltd., Osaka, Japan

[21] Appl. No.: 673,553

[22] Filed: Mar. 22, 1991

[30] Foreign Application Priority Data

Mar. 22, 1990 [JP] Japan .................................. 2-69570

[51] Int. Cl.$^5$ .................. C12P 17/18; C12P 17/14; C12P 17/02; C07D 281/10
[52] U.S. Cl. ..................................... 435/119; 435/120; 435/123; 435/135
[58] Field of Search ............... 435/123, 135, 119, 120; 540/491

[56] References Cited

U.S. PATENT DOCUMENTS

| | | | |
|---|---|---|---|
| 4,622,301 | 11/1986 | Gunther et al. | 435/135 |
| 4,734,367 | 3/1988 | Leuenberger et al. | 435/135 |

FOREIGN PATENT DOCUMENTS

| | | | |
|---|---|---|---|
| 144832 | 6/1985 | European Pat. Off. | |
| 0343714 | 11/1989 | European Pat. Off. | 435/123 |
| 0362556 | 4/1990 | European Pat. Off. | 435/123 |
| 60-58087 | 4/1985 | Japan. | |
| 60-202871 | 10/1985 | Japan. | |
| 0106391 | 3/1989 | Japan. | |
| 1-226881 | 9/1989 | Japan. | |
| 3-56471 | 3/1991 | Japan. | |
| 8907648 | 8/1989 | PCT Int'l Appl. | 435/135 |

OTHER PUBLICATIONS

Patent Abstracts of Japan, vol. 9, No. 188 (C-295)(1911), Aug. 3, 1985.
Patent Abstracts of Japan, vol. 13, No. 255, (C-606)(3603), Jun. 13, 1989.
Chemical Abstracts, vol. 112, No. 17, Apr. 23, 1990.

*Primary Examiner*—Herbert J. Lilling
*Attorney, Agent, or Firm*—Browdy and Neimark

[57] ABSTRACT

Disclosed is a process for preparing 2-halogeno-3-hydroxy-3-phenylpropionic acid ester compounds represented by the formula (I):

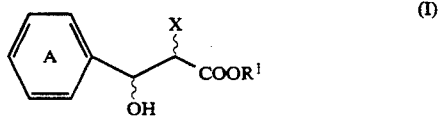

(I)

wherein Ring A is a phenyl group which may be substituted, $R^1$ is an ester residue, and X is a halogen atom, which comprises permitting an enzyme having the ability of stereoselectively reducing oxo group to hydroxy group to act on 2-halogeno-3-oxo-3-phenylpropionic acid ester compounds represented by the formula (II):

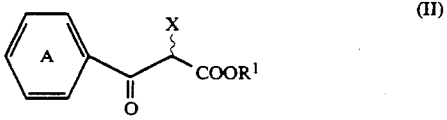

(II)

wherein Ring A, $R^1$ and X have the same meanings as defined above.

25 Claims, No Drawings

PROCESS FOR PREPARING 2-HALOGENO-3-HYDROXY-3-PHENYL-PROPIONIC ACID ESTER COMPOUNDS

BACKGROUND OF THE INVENTION

This invention relates to a novel process for preparing 2-halogeno-3-hydroxy-3-phenylpropionic acid ester compounds.

Optically active 2-halogeno-3-hydroxy-3-phenylpropionic acid ester compounds are important compounds as intermediates of diltiazem hydrochloride which is useful as a coronary vasodilating agent and other various pharmaceutical compounds.

In the prior art, as the process for preparing 2-halogeno-3-hydroxy-3-phenylpropionic acid ester compounds, there has been known the method in which a halogenoacetic acid ester compound and a benzaldehyde compound are permitted to react in the presence of an optically active lithium amide compound and alkyl lithium to give the above ester compounds (Japanese Unexamined Patent Publication NO. 226881/1989).

However, this process employs an expensive optically active reagent to effect asymmetric induction, when reacting the halogenoacetic acid ester compound and the benzaldehyde compound. Thus, there has been demanded a process for preparing 2-halogeno-3-hydroxy-3-phenylpropionic acid ester compounds by using an enzyme in place of an expensive optically active reagent.

SUMMARY OF THE INVENTION

The present inventors have studied intensively, and consequently found that 2-halogeno-2-hydroxy-3-phenylpropionic acid ester compounds can be obtained by permitting an enzyme having the ability of stereoselectively reducing oxo group to act on 2-halogeno-3-oxo-3-phenylpropionic acid ester compounds.

More specifically, according to the present invention, 2-halogeno-3-hydroxy-3-phenylpropionic acid ester compounds represented by the formula (I):

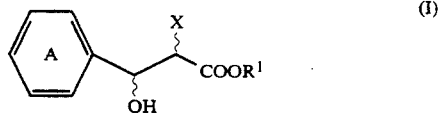

wherein Ring A is a phenyl group which may be substituted, $R^1$ is an ester residue, and X is a halogen atom, can be prepared by permitting an enzyme having the ability of stereoselectively reducing oxo group to hydroxy group to act on 2-halogeno-3-oxo-3-phenylpropionic acid ester compounds represented by the formula (II):

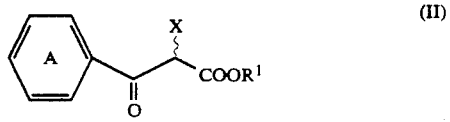

wherein Ring A, $R^1$ and X have the same meanings as defined above.

DESCRIPTION OF THE PREFERRED EMBODIMENTS

The process of the present invention can be practiced in the case when Ring A of the 2-halogeno-3-oxo-3-phenylpropionic acid ester compounds represented by the formula (II) is a phenyl group substituted, for example, with a lower alkyl group, a lower alkoxy group or a halogen atom as well as in the case when Ring A is unsubstituted phenyl group. The halogen atom represented by X is fluorine, chlorine, bromine or iodine atom. The ester residue represented by $R^1$ is generally a lower alkyl group, as exemplified by methyl group, ethyl group, isopropyl group or t-butyl group. Ring A is preferably a phenyl group substituted with a lower alkyl group or a lower alkoxy group, and $R^1$ is preferably a lower alkyl group.

According to the process of the present invention, by selecting an enzyme to be used suitably, a carbonyl group at the 3-position of the staring material (II) can be reduced stereoselectively to a hydroxymethylene group having an absolute configuration of R to obtain (2R, 3R) type and/or (2S, 3R) type desired products, or reduced to a hydroxymethylene group having an absolute configuration of S to obtain (2R, 3S) type and/or (2S, 3S) type desired products.

Further, among the enzymes to be used in the present method, there exist those which can reduce only one isomer of the substrate having either R or S absolute configuration at 2-position thereof (namely, 2R- or 2S-isomer) and produce stereoselectively a single isomer of the desired product having specified absolute configurations in both of two asymmetric carbon atoms at 2- and 3-positions thereof (namely, any one of 2R,3R-, 2R,3S-, 2S,3R- or 2S,3S-isomer).

The enzyme to be used in the present method includes reductase. Representative examples of the reductase may be those derived from microorganism, which may be extracted from microbial cells according to known methods. A culture broth of a microorganism producing the above-mentioned enzyme, microbial cells collected from said culture broth and a processed product of said microbial cells can be used as the enzyme sources.

Such microorganisms include yeasts, bacteria, molds and actinomycetes. Examples of the yeasts may include microorganisms belonging to the genus Candida, the genus Cryptococcus, the genus Hansenula, the genus Nematospora, the genus Rhodotorula, the genus Saccharomyces and the genus Zygosaccharomyces; examples of the bacteria include microorganisms belonging to the genus Arthrobacter; examples of the molds include microorganisms belonging to the genus Absidia, the genus Mucor and the genus Trichoderma; and examples of the actinomycetes include microorganisms belonging to the genus Mycobacterium and the genus Streptomyces, respectively.

As specific examples of such microorganism, there may be included, for example, *Candida maltosa* JCM 1504, Ditto IAM 12247, *Candida tropicalis* IFO 0589, Ditto IFO 1400, Ditto IFO 1647, Ditto IFO 1401, Ditto IFO 1404, *Cryptococcus laurentii* OUT 6027, *Hansenula anomalo* IFO 0118, Ditto IFO 0149, *Hansenula minuta* IFO 0975, *Hansenula nonfermentans* IFO 1473, *Nematospora coryli* IFO 0658, *Rhodotorula glutinis* IFO 0389, *Zygosaccharomyces rouxii* IFO 1814, *Arthrobacter protophormiae* IFO 12128, *Absidia corymbifera* IFO 4009, *Mucor ambiguus* IFO 6742, *Mucor angulimacros-*

*porus* IAM 6149, *Mucor circinelloides* IFO 6746, *Mucor fragilis* IFO 6449, *Mucor flavus* IAM 6143, *Mucor hiemalis* OUT 1045, Ditto IFO 6753, *Mucor janssenii* OUT 1050, *Muco javanicus* IFO 4569, Ditto IFO 4570, Ditto IFO 4572, *Mucor racemosus* IFO 4581, *Trichoderma viride* OUT 4283, Ditto OUT 4289, Ditto OUT 4642, Ditto OUT 4644, Ditto IFO 5720, Ditto IFO 31137, *Mycobacterium smegmatis* IFO 3154, *Mycobacterium phlei* IFO 3158, *Streptomyces olivochromogenes* IFO 3178 and *Saccharomyces cerevisiae* (a baker's yeast, manufactured by Oriental Kobo Kogyo K.K.).

These may be either wild strains or mutant strains, and further may be those derived from these microorganisms according to the bioengineering methods such as gene recombination and cell fusion.

Further, the culture broth and cells of the above microorganisms can be cultured in a medium for said microorganisms generally used in this field of the art, for example, in a conventional medium containing carbon sources, nitrogen sources and inorganic salts, at room temperature or under heating (preferably about 20° to 40° C.) and also under aerobic conditions at pH 2 to 8. If necessary, the cells can be obtained by separating and collecting from the culture broth according to a conventional method.

The enzyme to be employed in the present method may be used in the form of lyophilized cells and acetone dried cells of the above-mentioned microorganisms. Further, the microbial cells or treated cells can be also immobilized by known methods such as the polyacrylamide method, the sulfur-containing polysaccharide gel method (e.g., carrageenan gel method), the alginic acid gel method or the agar gel method, before use.

The stereoselective reduction reaction of the present invention can be practiced by permitting the enzyme to act on 2-halogeno-3-oxo-3-phenylpropionic acid ester compounds (II).

The substrate concentration may be generally 0.1 to 20%, particularly preferably 0.2 to 10%, and the reaction can proceed at normal temperature or under heating, preferably at 10° to 50° C., particularly preferably at 25° to 40° C. During the reaction, it is preferred to adjust the pH of the reaction mixture to 2 to 6, above all 3 to 5. In this case, since many substrates are difficultly soluble in water, a small amount of a water miscible organic solvent, for example, dimethylformamide or a lower alkanol such as methanol and ethanol may be used as a dissolving aid. Further, the reaction can be practiced in an aqueous solution, an organic solvent or a two-phase solvent of an aqueous solvent and an organic solvent. As such an organic solvent, there may be included water-immiscible organic solvents, for example, an aromatic solvent such as benzene or toluene; and alkane such as n-hexane; an ether solvent such as diethyl ether or diisopropyl ether; and an ester solvent such as ethyl acetate.

After completion of the reaction, the reaction mixture is extracted with an organic solvent such as toluene, chloroform and ethyl acetate, and the organic layer is condensed and applied to chromatography or distillation to obtain optically active 2-halogeno-3-hydroxy-3-phenylpropionic acid ester compounds (I).

The 2-halogeno-3-hydroxy-3-phenylpropionic acid ester compounds (I) thus obtained can be converted to corresponding 3-phenylglycidates by intramolecular ring closure reaction in an appropriate solvent (e.g., a lower alkanol) under the presence of a base (e.g., an alkali metal alkoxide) at −10° to 50° C., preferably 0° C. to room temperature.

During the reaction, since the 3S type desired products, i,e., (2R, 3S) type and 2S, 3S) type desired products, form a trans-(2R, 3S) type glycidate by intramolecular ring closure reaction regardless of the absolute configuration of the 2-position, the above products are used for synthesizing diltiazem hydrochloride as shown below.

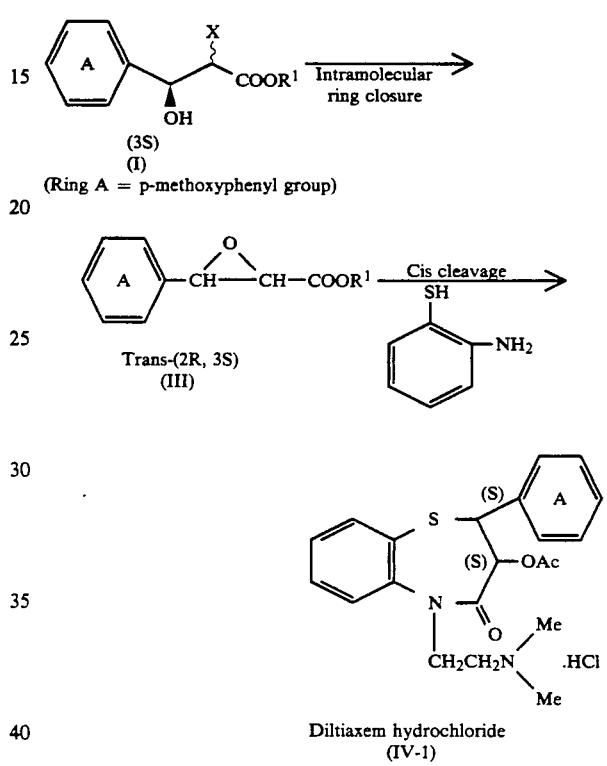

On the other hand, since the 3R type desired products, i.e., (2R, 3R) type and (2S, 3R) type desired products, form a trans-(2S,3R) type glycidate by intramolecular ring closure reaction regardless of the absolute configuration of the 2-position, the above products are used for synthesizing a benzothiazepine compound disclosed in, for example, Japanese Unexamined Patent Publication No. 202871/1985 as shown below.

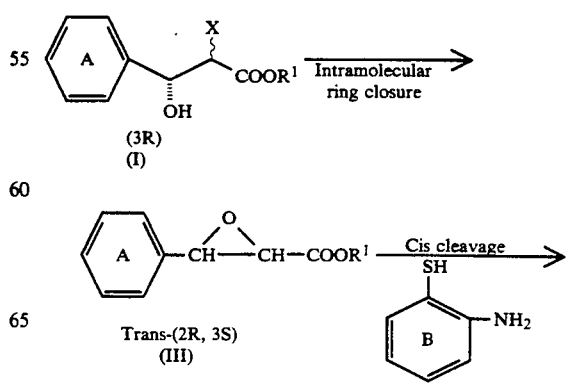

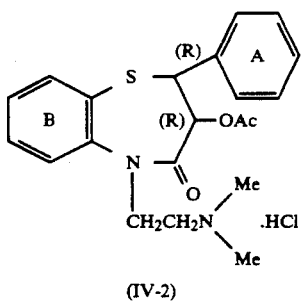

(IV-2)

In the above formulae, Ring A and Ring B each represent a benzene ring which may be substituted.

The 2-halogeno-3-oxo-3-phenylpropionic acid ester compounds (II) which are the starting material of the present invention can be prepared by reacting the acetophenone compound represented by the following formula:

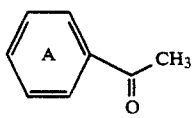

wherein Ring A has the same meanings as defined above, with a di-lower alkyl carbonate in an appropriate solvent (e.g., ethers and aromatic hydrocarbons) under the presence of a base (e.g., an alkali metal or an alkali metal hydride) to prepare 3-oxo-3-phenylpropionic acid ester compounds represented by the following formula:

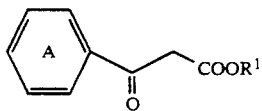

wherein Ring A and $R^1$ have the same meanings as defined above, and then reacting the esters obtained with a halogenating agent (e.g., sulfuryl halide or N-halosuccinimide).

The above-mentioned process of the present invention can easily prepare (3R) or (3S) type 2-halogeno-3-hydroxy-3-phenylpropionic acid ester compounds (I) without necessity of using an expensive optically active reagent and yet without complicated steps, and therefore, it can be an industrially advantageous preparation process.

EXAMPLES

The present invention is described below in detail by referring to Examples and Reference examples.

EXAMPLE 1

Each 100 ml of a medium (adjusted pH to 6.5 with 0.1N-sodium hydroxide) containing 5% of flucose, 0.1% of potassium dihydrogen phosphate, 0.1% of ammonium sulfate, 0.05% of urea, 0.05% of magnesium sulfate heptahydrate, 0.05% of calcium chloride dihydrate, 0.1% of yeast extract, 0.0002% of ferrous sulfate heptahydrate, 0.0002% of manganese chloride tetrahydrate and 0.0002% of zinc sulfate heptahydrate was charged in 29 shaking flasks having a volume of 500 ml, respectively, and sterilized at 120° C. for 10 minutes. A platinum loop of *Mucor ambiguus* IFO 6742 was inoculated into 100 ml of the same media and the inoculated media was cultured at 30° C. for 72 hours. One ml of the culture broth was poured into each of the sterilized media contained in 29 flasks and the mixture were further shaken at 30° C for 72 hours.

The cells collected by filtration with a sterilized gauze from the above culture broths were suspended in 100 ml of a McIlvaine buffer (pH 5.0) containing 5% of glucose, respectively, and further to each shaking flask was added 0.2 ml of dimethylformamide containing 200 mg of methyl 2-chloro-3-oxo-3(p-methoxyphenyl)propionate, followed by shaking reaction at 30° C. for 24 hours.

After these reaction mixtures were collected and 2,900 ml of ethyl acetate was added thereto, the cells were removed by filtration and an organic layer was separated, followed further by extraction of an aqueous layer again with 2,900 ml of ethyl acetate. The organic layers were mixed, washed with saturated saline solution, and dried. Subsequently, the solvent was evaporated under reduced pressure. Purification was carried out by silica gel chromatography (solvent: n-hexane/-chloroform/ethyl acetate=4/1/1) to obtain 2,320 mg of methyl (2S, 3R)-2-chloro-3-hydroxy-3-(p-methoxyphenyl)propionate.

The absolute configuration of the desired product isolated was determined according to the method in Reference example 1.

$[\alpha]_D^{23} + 15.5°$ (c=1.023, methanol)

NMR $\delta$(CDCl$_3$):

2,89 (1H, d, J=3.9 Hz, OH), 3.67, 3.80 (3Hx2, sx2, OCH$_3$, CO$_2$CH$_3$), 4.42 (1H, d, J=6.8 Hz, —CHCl), 5.08 (1H, d of d, J=6.8 Hz, 3.9 Hz, —CHOH), 6.89 (2H, d, J=8.8 Hz), 7.30 (2H, d, J=8.8 Hz)

IR (Nujol) $\nu cm_{max}^{-1}$: 3520, 1745, 1615, 1515, 1250, 1170, 1030, 825

MS(m/e): 244 (M$^+$)

m.p.: 103° to 103.5° C.

Optical purity syn* (2S, 3R) isomer: >99% e.e.

* In the present specification, syn and anti are indicated according to the definition by Masamune eta al described in Angew. Chem. Int. Ed., Vol. 19, pp. 557 to 558 (1980).

EXAMPLE 2

A platinum loop of *Nematospora coryli* IRO 0658 was inoculated in the same media as Example 1 in place of *Mucor ambiguus* and the inoculated media was cultured at 30° C. for 24 hours. 1 ml of the culture broth was poured into each of 29 flasks containing the same media as mentioned above and the mixtures were further shaken at 30° C. for 24 hours.

The cells were collected from the above culture broths, and then reaction, extraction and purification were carried out in the same manner as in Example 1 to obtain 300 mg of a mixture of methyl (2S, 3S) and (2R, 3S)-2-chloro-3-hydroxy-3-(p-methoxyphenyl)propionates.

The absolute configuration was determined according to the method in Reference example 1.

NMR $\delta$ (CDCl$_3$): anti; isomer:syn iosmer=1:2

Anti isomer: 2.89 (1H, d, J=4.6 Hz, OH), 3.80 (6H, s, OCH$_3$, CO$_2$CH $_3$), 4.36 (1H, d, J=8.1 Hz, —CHCl), 5.00 (1H, d of d, J=8.1 Hz, 4.6 Hz, —CHOH), 6.91 (2H, d, J=8.8 Hz), 7.32 (2H, d, J=8.8 Hz)

Syn isomer: 2.89 (1H, d, J=3.9 Hz, O$\underline{H}$), 3.67, 380 (3Hx2, sx2, OCH$_3$, CO$_2$CH$_3$), 4.42 (1H, $\underline{d}$, J=6.8 Hz, —CHCl), 5.08 (1H, d of d, J=6.8 Hz, 3.9 Hz, —C$\underline{H}$OH), 6.89 (2H, d, J=8.8 Hz), 7.30 (2H, d, J=8.8 Hz)

IR (Nujol) $\nu cm_{max}^{-1}$: 35,20, 3450, 1745, 1730, 1615, 1515, 1250, 1170, 1030, 825

MS(m/e): 244 (M+)

Optical purity anti (2S, 3S) isomer: 87% e.e.
syn (2R, 3S) isomer: 96% e.e.

EXAMPLE 3

3 ml of the same medium (pH 6.5) as in Example 1 was charged into a test tube with an outer diameter of 15 mm, and sterilized at 120° C. for 10 minutes. Into the medium was inoculated a platinum loop of a yeast shown in Table 1 below, and the yeast was subjected to shaking culture at 30° C. for 24 hours. The cells collected by centrifugation from the above culture broth were suspended in 3 ml of a McIlvaine buffer (pH 5.0) containing 5% of glucose, and 6 μl of dimethylformamide containing 6 mg of methyl 2-chloro-3-oxo-3-(p-methoxyphenyl)propionate was charged thereinto, followed by shaking reaction at 30° C. for 24 hours. Then, the reaction mixture was extracted with 2 ml of ethyl acetate and then the amount of methyl 2-chloro-3-hydroxy-3-(p-methoxyphenyl) propionate formed was quantitated. Quantitation was performed by high performance liquid chromatography by use of a ZORBAX CN (trade name) 4.6 mmϕ×250 mm manufactured by Du Pont Instruments and marketed by Shimadzu Corporation. The absolute configuration of the desired product isolated by thin layer chromatography (silica gel, solvent: n-hexane/chloroform/ethyl acetate=4/1/1) was determined according to the method in Reference example 1.

In Table 1, the amount formed and optical purity thereof are shown.

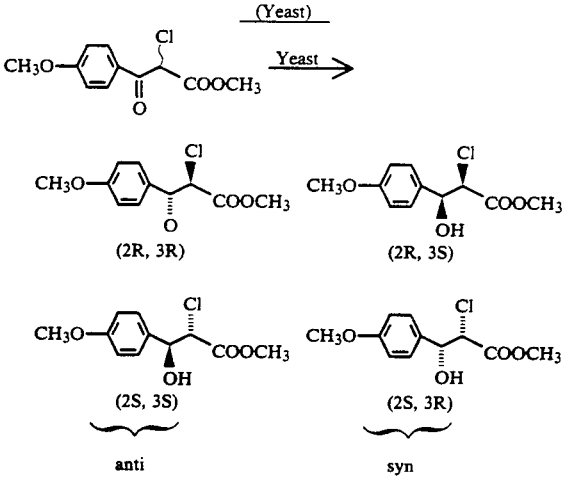

TABLE 1

(Yeast)

| Microorganism used | Amount formed (mg) | anti/syn | Optical purity (% e.e.) | |
|---|---|---|---|---|
| Candida maltosa JCM 1504 | 0.8 | 77/23 | anti (2R, 3R): | 37 |
| | | | syn (2S, 3R): | 75 |
| Candida maltosa IAM 12247 | 0.6 | 73/27 | anti (2R, 3R): | 36 |
| | | | syn (2S, 3R): | 53 |
| Candida tropicalis IFO 0589 | 0.1 | 28/72 | anti (2R, 3R): | 12 |
| | | | syn (2S, 3R): | 91 |

TABLE 1-continued (Yeast)

Methyl 2-chloro-3-hydroxy-3-(p-methoxyphenyl)propionate

| Microorganism used | Amount formed (mg) | anti/syn | Optical purity (% e.e.) | |
|---|---|---|---|---|
| Candida tropicalis IFO 1400 | 0.1 | 84/16 | anti (2R, 3R): | >99 |
| | | | syn (2S, 3R): | >99 |
| Candida tropicalis IFO 1647 | 0.2 | 82/18 | anti (2R, 3R): | 35 |
| | | | syn (2S, 3R): | 60 |
| Candida tropicalis IFO 1401 | 0.3 | 72/28 | anti (2R, 3R): | 46 |
| | | | syn (2S, 3R): | 90 |
| Candida tropicalis IFO 1404 | 0.1 | 95/5 | anti (2R, 3R): | >99 |
| | | | syn (2S, 3R): | 65 |
| Cryptococcus laurentii OUT 6027 | 2.6 | 80/20 | anti (2R, 3R): | >99 |
| | | | syn (2S, 3R): | 99 |
| Hansenula anomala IFO 0118 | 0.2 | 86/14 | anti (2R, 3R): | 3 |
| | | | syn (2S, 3R): | 78 |
| Hansenula anomala IFO 0149 | 0.4 | 87/13 | anti (2R, 3R): | 63 |
| | | | syn (2S, 3R): | >99 |
| Hansenula minuta IFO 0975 | 1.5 | 63/37 | anti (2R, 3R): | 99 |
| | | | syn (2S, 3R): | 97 |
| Hansenula nonfermentans IFO 1473 | 0.8 | 47/53 | anti (2R, 3R): | >99 |
| | | | syn (2S, 3R): | 98 |
| Zygosaccharomyces rouxii IFO 1814 | 0.6 | 51/49 | anti (2S, 3S): | 91 |
| | | | syn (2R, 3S): | 92 |
| Rhodotorula glutinis IFO 0389 | 0.8 | 1/99 | syn (2R, 3S): | 96 |

EXAMPLE 4

A medium (adjusted pH to 7.0 with 0.1N-sodium hydroxide) containing 1% of glucose, 1% of peptone, 0.1% of potassium dihydrogen phosphate, 0.1% of ammonium sulfate, 0.05% of urea, 0.05% of magnesium sulfate heptahydrate, 0.05% of calcium chloride.dihydrat, 0.1% of yeast extract, 0.0002% of ferrous sulfate.heptahydrate, 0.0002% of manganese chloride.tetrahydrate and 0.0002 % of zinc sulfate.heptahydrate was charged into a test tube with an outer diameter of 15 mm, and sterilized at 120° C. for 10 minutes. In the same manner as in Example 3, a platinum loop of a bacterium shown in Table 2 below was inoculated, and the bacterium was subjected to shaking culture for 24 hours. Also in the same manner, reaction, extraction and quantitation were carried out.

In Table 2, the amount formed and optical purity thereof are shown.

TABLE 2

| | (Bacterium) | | |
|---|---|---|---|
| | Methyl 2-chloro-3-hydroxy-3-(p-methoxyphenyl)propionate | | |
| Microorganism used | Amount formed (mg) | anti/syn | Optical purity (% e.e.) |
| *Arthrobacter protophormiae* IFO 12128 | 0.1 | >99/1 | anti (2S, 3S): >99 |

EXAMPLE 5

In the same manner as in Example 3, a platinum loop of a mold shown in Table 3 below was inoculated, and the mold was subjected to shaking culture for 72 hours. Also in the same manner, reaction, extraction and quantitation were carried out.

In Table 3, the amount formed and optical purity thereof are shown.

TABLE 3

| | (Mold) | | |
|---|---|---|---|
| | Methyl 2-chloro-3-hydroxy-3-(p-methoxyphenyl)propionate | | |
| Microorganism used | Amount formed (mg) | anti/syn | Optical purity (% e.e.) |
| *Absidia corymbifera* IFO 4009 | 1.1 | 1/>99 | syn (2S, 3R): >99 |
| *Mucor angulimacrosporus* IAM 6149 | 0.8 | 11/89 | anti (2R, 3R): >99<br>syn (2S, 3R): >99 |
| *Mucor circinelloides* IFO 6746 | 0.5 | 1/>99 | syn (2S, 3R): >99 |
| *Mucor fragilis* IFO 6449 | 0.2 | 1/>99 | syn (2S, 3R): >99 |
| *Mucor flavus* IAM 6143 | 0.3 | 15/85 | anti (2R, 3R): 72<br>syn (2S, 3R): 98 |
| *Mucor hiemalis* OUT 1045 | 1.2 | 12/88 | anti (2R, 3R): 68<br>syn (2S, 3R): >99 |
| *Mucor janssenii* OUT 1050 | 1.4 | 5/95 | anti (2R, 3R): >99<br>syn (2S, 3R): >99 |
| *Mucor javanicus* IFO 4569 | 1.7 | 7/93 | anti (2R, 3R): >99<br>syn (2S, 3R): >99 |
| *Mucor javanicus* IFO 45709 | 2.4 | 7/93 | anti (2R, 3R): >99<br>syn (2S, 3R): >99 |
| *Mucor javanicus* IFO 4572 | 0.2 | 1/>99 | syn (2S, 3R): >99 |
| *Mucor racemosus* IFO 4581 | 0.7 | 18/82 | anti (2R, 3R): 36<br>syn (2S, 3R): 99 |
| *Mucor hiemalis* IFO 6753 | 1.4 | 8/92 | anti (2R, 3R): 27<br>syn (2S, 3R): >99 |
| *Trichoderma viride* OUT 4283 | 2.2 | 38/62 | anti (2S, 3S): 80<br>syn (2R, 3S): 94 |
| *Trichoderma viride* OUT 4289 | 2.5 | 36/64 | anti (2S, 3S): 85<br>syn (2R, 3S): 81 |
| *Trichoderma viride* OUT 4642 | 3.5 | 44/56 | anti (2S, 3S): 87<br>syn (2R, 3S): 96 |
| *Trichoderma viride* OUT 4644 | 0.4 | 75/25 | anti (2S, 3S): 97<br>syn (2R, 3S): 68 |
| *Trichoderma viride* IFO 5720 | 2.5 | 41/59 | anti (2S, 3S): 82<br>syn (2R, 3S): 91 |
| *Trichoderma viride* IFO 31137 | 1.3 | 37/63 | anti (2S, 3S): 78<br>syn (2R, 3S): 96 |

EXAMPLE 6

By using a medium having the same composition as in Example and having pH adjusted to 7.3 with 0.1N sodium hydroxide, in the same manner as in Example 3, a platinum loop of an actinomycete shown in Table 4 below was inoculated, and the actinomycete was subjected to shaking culture at 30° C. for 72 hours. Also in the same manner, reaction, extraction and quantitation were carried out.

In Table 4, the amount formed and optical purity thereof are shown.

TABLE 4

| | (Actinomycete) | | |
|---|---|---|---|
| | Methyl 2-chloro-3-hydroxy-3-(p-methoxyphenyl)propionate | | |
| Microorganism used | Amount formed (mg) | anti/syn | Optical purity (% e.e.) |
| *Mycobacterium smegmatis* IFO 3154 | 0.1 | 82/18 | anti (2R, 3R): 53<br>syn (2S, 3R): 22 |
| *Mycobacterium phlei* IFO 3158 | 0.5 | 76/24 | anti (2S, 3S): 56<br>syn (2R, 3S): 31 |
| *Streptomyces olivochromogenes* IFO 3178 | 0.3 | >99/1 | anti (2S, 3S): 92 |

EXAMPLE 7

In a test tube with an outer diameter of 15 mm, 0.25 g of a baker's yeast (*Saccharomyces cerevisiae*, manufactured by Oriental Kobo Kogyo K K ) was suspended in 3 ml of a McIlvaine buffer containing 0.54 g of glucose dissolved therein, and then 6 μl of dimethylformamide containing 6 mg of methyl 2-chloro-3-oxo-3-(p-methoxyphenyl)propionate was charged, followed by shaking reaction at 30° C. for 24 hours. When the reaction mixture was extracted with 2 ml of ethyl acetate and the amount of methyl 2-chloro-3-hydroxy-3-(p-methoxyphenyl)propionate formed was quantitated, it was found that 0.6 mg of the product was formed.

In this case, the forming ratio of anti isomer to syn isomer and optical purity thereof are shown below.

Forming ratio: anti/syn=62/38
Optical purity: anti (2R, 3R) isomer:>99 % e.e.
syn (2S, 3R) isomer:>99 % e.e.

REFERENCE EXAMPLE 1

Condensation reaction between p-anisaldehyde and methyl chloroacetate was effected in tetrahydrofuran at −78° C. in the presence of lithium diisopropylamide, and the methyl 2-chloro-3-hydroxy-3-(p-methoxyphenyl)propionate obtained was separated into anti isomer (a mixture of (2R, 3R) isomer and (2S, 3S) isomer) and syn isomer (a mixture of (2R, 3S) isomer and (2S, 3R) isomer) by silica gel chromatography (solvent: n-hexane/ethyl acetate=3/1). NMR of these isomers was measured to determine anti isomer and syn isomer. When these isomers were analyzed by high performance liquid chromatography by use of a chiralcel OJ 4.6 mmφ×250 mm manufactured by Dicel Chemical Industries, LTD. (mobile phase: n-hexane/i-propanol=7/3, flow rate: 1.0 ml/min, column temperature: 40° C.), a retention time of the anti isomer was 9.2 minutes and 9.9 minutes, and a retention time of the syn isomer was 11.7 minutes and 13.9 minutes.

The absolute configuration of the methyl 2-chloro-3-hydroxy-3-(p-methoxyphenyl)propionate obtained in Example 1 was determined to be (2S, 3R) isomer since it had a retention time of 13.9 minutes, and it could be induced to methyl (2S, 3R)-3-(p-methoxyphenyl)glycidate by ring closure with sodium methylate in a methanol solution. Further, the methyl 2-chloro-3-hydroxy-3-(p-methoxyphenyl)propionate obtained in Example 2 was applied to silica gel chromatography (solvent: n-hexane/chloroform/ethyl acetate =4/1/1) to give mainly two compounds which have retention times of 9.9 and 11.7 minutes, respectively in the above high performance liquid chromatography. Both of these compounds could be induced to methyl (2R, 3S)-3-(p-methoxyphenyl)-glycidate by ring closure with sodium methylate in a methanol solution.

Accordingly, the relationship between the retention time obtained by the above high performance liquid chromatography and the absolute configuration of methyl 2-chloro-3-hydroxy-3-(p-methoxyphenyl)propionate was defined as follows.

(2R, 3R) isomer: 9.2 minutes
(2S, 3S) isomer: 9.9 minutes
(2R, 3S) isomer: 11.7 minutes
(2S, 3R) isomer: 13.9 minutes

REFERENCE EXAMPLE 2

(1) 30.7 g of sodium was added to 300 ml of toluene, and the mixture was heated to 93° C., followed by cooling while vigorous stirring, to give sandy products. To the product, 600 ml of toluene containing 300 g of dimethyl carbonate was added, and further 250 ml of a toluene solution containing 100 g of p-methoxyacetophenone was added dropwise over 2 hours and 15 minutes at 84° to 86° C. After the dropwise addition, the mixture was stirred under heating at 82° to 83° C. for 1.5 hours, and then the solvent was evaporated. To the residue was added 1 l of isopropyl ether, and crystals were collected by filtration and washed with 500 ml of isopropyl ether. These crystals were added to a mixture of ice and ethyl acetate containing 100 g of acetic acid, and extracted with ethyl acetate. The extract was washed with 5 % sodium hydrogen carbonate and then with water, and dried. Subsequently, the solvent was evaporated to obtain 131.6 g of methyl 3-oxo-3-(p-methoxyphenyl)propionate as an oily product.

IR (liquid) $vcm_{max}^{-1}$: 3625 to 3450, 1740, 1655
NMR $\delta$(CDCl$_3$):
3.74 (3H, s), 3.87 (3H, s), 3.95 (2H, s), 6.94 (2H, d, J=9.2 Hz), 7.92 (2H, d, J=9.2 Hz)

(2) 131 g of the methyl 3-oxo-3-(p-methoxyphenyl)propionate obtained in the above (1) was dissolved in 1.3 l of tetrachloromethane, and to the solution was added dropwise 85 g of sulfuryl chloride at 45° to 50° C. over 1 hour. After the dropwise addition, the mixture was stirred at the same temperature for 1 hour, cooled, washed with water and dried. Subsequently, the oily product of the residue obtained by evaporation of the solvent was distilled under reduced pressure to obtain 140 g of methyl 2-chloro-3-oxo-3-(p-methoxyphenyl)propionate.

b.p.: 143.5° to 145° C./0.3 mmHg
IR (liquid) $vcm_{max}^{-1}$ 1750, 1660
NMR $\delta$(CDCl$_3$):
3.82 (3H, s), 3.88 (3H, s), 5.91 (1H, s), 6.96 (2H, d, J=9.0 Hz), 7.97 (2H, d, J=9.0 Hz)

REFERENCE EXAMPLE 3

(1) In a suspension containing 1.614 g of N,N'-dibenzoyl-L-cystine, 357 mg of t-butanol and 20 ml of tetrahydrofuran, 16 ml of a tetrahydrofuran solution containing 237 mg of lithium borohydride was added under argon atmosphere, and the mixture was refluxed for 1 hour. Subsequently, 10 ml of a tetrahydrofuran solution containing 728 mg of methyl 2-chloro-3-oxo-3-(p-methoxyphenyl)propionate was added at −65° to −70° C., and the mixture was stirred at the same temperature for 1 hour. After the reaction, the reaction mixture was decomposed with addition of 10% hydrochloric acid, and then the pH was adjusted to 9 to 10 with addition of a 5% aqueous sodium hydrogen carbonate solution, followed by extraction with ethyl ether. After the extract was washed with water and dried, the solvent was evaporated. 740 mg of the yellow oily product of the residue obtained was purified by silica gel column chromatography (solvent: hexane/ethyl acetate =3/1) to obtain 660 mg of a mixture of syn (2R, 3S) isomer and anti (2S, 3S) isomer of methyl 2-chloro-3-hydroxy-3-(p-methoxyphenyl)propionate as a colorless crystal.

IR (liquid) $vcm_{max}^{-1}$: 3480, 1750, 1610, 1515, 1250, 1175, 1030, 830
NMR $\delta$(CDCl$_3$):
syn isomer: 2.89 (1H, d, 3.9 Hz), 3.67 (3H, s), 3.80 (3H, s), 4.42 (1H, d, 6.8 Hz), 5.08 (1H, dd, 3.9 and 6.8 Hz), 6.89 (2H, d, 8.8 Hz), 7.30 (2H, d, 8.8 Hz)
anti isomer: 2.89 (1H, d, 4.6 Hz), 3.80 (6H, s), 4.35 (1H, d, 8.1 Hz), 5.00 (1H, dd, 4.6 and 8.1 Hz), 6.91 (2H, d, 8.8 Hz), 7.32 (2H, d, 8.8 Hz)

(2) To a solution containing the crystals obtained in the above (1) dissolved in 16 ml of methanol was added a methanol solution containing 153 mg of sodium methylate at 0° C., and the mixture was stirred at the same temperature for 90 minutes, followed by stirring at room temperature for 10 minutes. Subsequently, water was added to the reaction mixture, and extraction was effected with ethyl ether. After the extract was washed with saturated saline solution and dried, the solvent was evaporated. The oily product of the residue obtained was purified by silica gel column chromatography (solvent: hexane/ethyl acetate =3/1) to obtain 506 mg of methyl (2R, 3S)-3-(p-methoxyphenyl)glycidate.

$[\alpha]_D^{20}$ −143.5 (c=0.30, methanol)
(Optical purity: 82% e.e.; by HPLC)
IR (Nujol) $vcm_{max}^{-1}$: 2920, 1730, 1615, 1520, 1440, 1250, 1030, 840
NMR $\delta$(CDCl$_3$):
3.50 (1H, d, J=1.8 Hz), 3.80 (3H, s), 3.81 (3H, s), 4.04 (1H, d, J=1.8 Hz), 6.87 (2H, d, J=9.0 Hz), 7.20 (2H, d, J=9.0 Hz)
Mass (m/e): 208 (M$^+$)

We claim:

1. A process for preparing a 3R or 3S-2-chloro-3-hydroxy-3-phenyl-propionic acid ester compound represented by the formula (I):

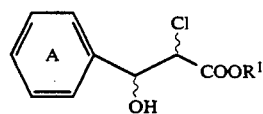

(I)

wherein Ring A is a phenyl group which may be substituted and R$^1$ is an ester residue,
which comprises permitting an enzyme having the ability of enantioselectively reducing an oxo group to a hydroxy group to act on a 2-chloro-3-oxo-3-phenylpropionic acid ester compound represented by the formula (II):

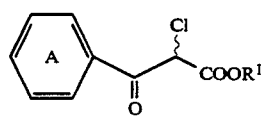

(II)

wherein Ring A and R$^1$ have the same meanings as defined above.

2. The process according to claim 1, wherein the enzyme is a reductase.

3. The process according to claim 2, wherein the reductase is derived from the microorganisms belonging to the genus selected from the group consisting of the genus Candida, the genus Cryptococcus, the genus Hansenula, the genus Nematospora, the genus Rhodotorula, the genus Saccharomyces, the genus Zygosaccharomyces, the genus Arthrobacter, the genus Absidia, the genus Mucor, the genus Trichoderma, the genus Mycobacterium and the genus Streptomyces.

4. The process according to claim 1, wherein Ring A is a lower alkylphenyl group or a lower alkoxyphenyl group, and $R^1$ is a lower alkyl group.

5. The process according to claim 4, wherein Ring A is a lower alkoxyphenyl group.

6. The process according to claim 5, wherein the 2-chloro-3-hydroxy-3-phenylpropionic acid ester compounds are lower alkyl esters of 2-chloro-3-hydroxy-3-(p-methoxyphenyl)propionic acid.

7. The process according to claim 1, wherein said stereoselective reduction is carried out in a substrate concentration of 0.1 to 20% at normal temperature or under heating and at a pH of 2 to 6.

8. The process according to claim 7, wherein said reduction is carried out in a substrate concentration of 0.2 to 10% at a temperature of 10° to 50° C. and a pH of 3 to 5.

9. The process according to claim 1, wherein the reaction is carried out in an aqueous solution, an organic solvent or a two-phase solvent system of aqueous solution and organic solvent.

10. The process according to claim 1, wherein said enzyme is selected so as to have the ability to enantioselectively reduce the oxo group to a hydroxy group of the absolute configuration of R and wherein the 3-position of the product compound has an absolute configuration of R.

11. The process according to claim 1, wherein said enzyme is selected so as to have the ability to enantioselectively reduce the oxo group to a hydroxy group of the absolute configuration of S. and wherein the 3-position of the product compound has an absolute configuration of S.

12. The process according to claim 10, wherein said enzyme is a reductase derived from a microorganism belonging to a genus selected from the group consisting of the genus Candida, the genus Cryptococcus, the genus Hansenula, the genus Saccharomyces, the genus Absidia and the genus Muco.

13. The process according to claim 11, wherein said enzyme is a reductase derived from a microorganism belonging to a genus selected form the group consisting of the genus Nematospora, the genus Rhodotorula, the genus Zygosaccharomyces, the genus Arthrobacter, the genus Trichoderma and the genus Streptomyces.

14. A process for preparing an optically active benzothiazepine compound represented by the formula (IV):

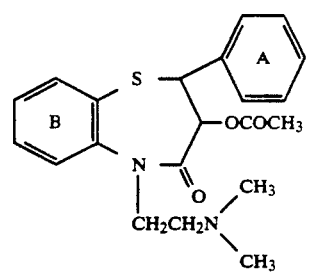

wherein Rings A and B are phenyl groups which may be substituted, comprising the steps of:

permitting an enzyme having the ability of enantioselectively reducing an oxo group to a hydroxy group to act on a 2-chloro-3-oxo-3-phenylpropionic acid ester compound represented by the formula (II):

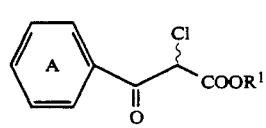

wherein Ring A has the same meaning as defined above and $R^1$ is an ester residue, so as to form an optically active 2-chloro-3-hydroxy-3-phenylpropionic acid ester compound represented by the formula (I):

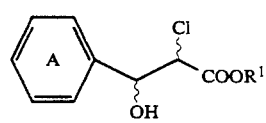

subjecting said compound of formula (I) to intramolecular ring closure to form an optically active compound of formula (III):

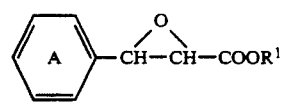

and reacting said compound of formula (III) with a compound of the formula

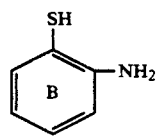

under appropriate conditions to form the benzothiazepine compound of formula IV.

15. A process for preparing a benzothiazepine compound represented by the formula (IV-1)

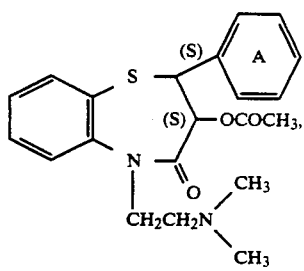

(IV-1)

wherein Ring A is a phenyl group which may be substituted, comprising the steps of:

permitting an enzyme having the activity of enantioselectively reducing an oxo group to a hydroxy group of the absolute configuration of S, to act on a 2-chloro-3-oxo-3-phenylpropionic acid ester compound represented by the formula

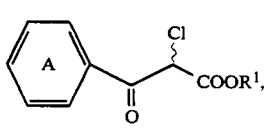

(II)

wherein $R^1$ is an ester residue, so as to form an optically active (2R, 3S)-type and/or (2S, 3S)-type 2-chloro-3-hydroxy-3-phenylpropionic acid ester compound represented by the formula (I-1):

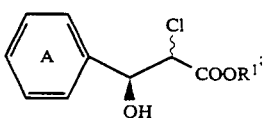

(I-1)

subjecting said compound of formula (I-1) to intramolecular ring closure to form an optically active trans-(2R, 3S) compound of formula (III-1):

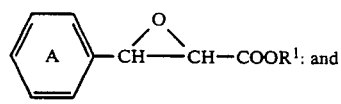

(III-1)

reacting said compound of formula (III-1) with a compound of the formula:

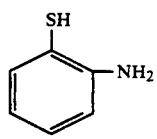

under appropriate conditions to form the benzothiazepine compound of formula (IV-1).

16. The process according to claim 15, wherein Ring A is a lower alkoxyphenyl group.

17. A process for preparing a benzothiazepine compound represented by the formula (IV-2):

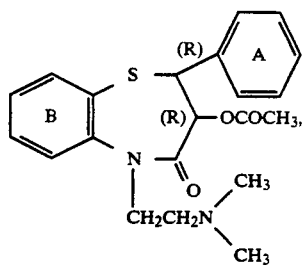

(IV-2)

wherein Ring A and Ring B each is a phenyl group which may be substituted, comprising the steps of:

permitting an enzyme having the activity of enantioselectively reducing an oxo group to a hydroxy group of the absolute configuration of R, to act on a 2-chloro-3-oxo-3-phenylpropionic acid ester compound represented by the formula (II):

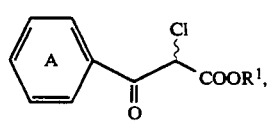

(II)

wherein $R^1$ is an ester residue, so as to form an optically active (2R,3R)-type and/or (2S, 3R)-type 2-chloro-3-hydroxy-3-phenylpropionic acid ester compound represented by the formula (I-2):

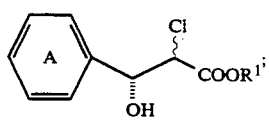

(I-2)

subjecting said compound of formula (I-2) to intramolecular ring closure to form an optically active trans(2R,3S) compound of formula (III-2):

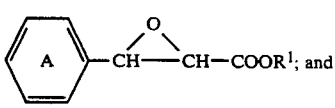

(III-2)

reacting said compound of formula (III-2) with a compound of the formula:

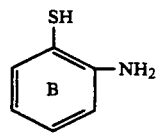

under appropriate conditions to form the benzothiazepine compound of formula (IV-2).

18. The process according to claim 17, wherein Ring A is a lower alkoxyphenyl group, and Ring B is a chloro phenyl group.

19. The process according to claim 17, wherein Ring A and Ring B each is a lower alkylphenyl group.

20. The process according to claim 14, wherein Ring A is a lower alkoxyphenyl group, and Ring B is a phenyl group.

21. The process according to claim 14, wherein Ring A is a lower alkoxyphenyl group, and Ring B is a chlorophenyl group.

22. The process according to claim 14, wherein Ring A and Ring B each is a lower alkylphenyl group.

23. A process for preparing trans-3-phenylglycidates represented by the formula (III):

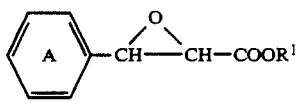

wherein Ring A is a phenyl group which may be substituted and $R^1$ is an ester residue,
which comprises permitting an enzyme having the ability of enantioselectively reducing an oxo group to a hydroxy group to act on a 2-chloro-3-oxo-3-phenylpropionic acid ester compound represented by the formula (II):

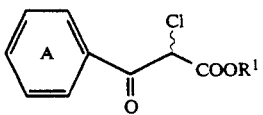

wherein Ring A and $R^1$ are the same meanings as defined above,
to give a 2-chloro-3-hydroxy-3-phenylpropionic acid ester compound represented by the formula (I):

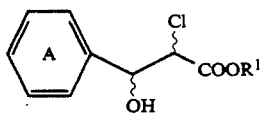

wherein Ring A and $R^1$ are the same meanings as defined above,
and subjecting the thus-obtained compound (I) to an intramolecular ring closure reaction.

24. The process according to claim 23, wherein Ring A is a lower alkylphenyl group or a lower alkoxyphenyl group, and $R^1$ is a lower alkyl group.

25. The process according to claim 24, wherein Ring A is a lower alkoxyphenyl group.

* * * * *